US005394452A

United States Patent [19]
Swerdloff et al.

[11] Patent Number: 5,394,452
[45] Date of Patent: Feb. 28, 1995

[54] VERIFICATION SYSTEM FOR RADIATION THERAPY

[75] Inventors: Stuart Swerdloff; Thomas R. Mackie; Timothy Holmes, all of Madison, Wis.

[73] Assignee: Wisconsin Alumni Research Foundation, Madison, Wis.

[21] Appl. No.: 74,185

[22] Filed: Jun. 9, 1993

Related U.S. Application Data

[63] Continuation-in-part of Ser. No. 854,521, Mar. 19, 1992.

[51] Int. Cl.$^6$ .............................................. A61N 5/10
[52] U.S. Cl. ........................................ 378/65; 378/150
[58] Field of Search ........................... 378/65, 150-153

[56] References Cited

U.S. PATENT DOCUMENTS

| | | | |
|---|---|---|---|
| 4,754,147 | 6/1988 | Maughan et al. | 250/505.1 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/158 |
| 4,987,309 | 1/1991 | Klasen et al. | 250/492.1 |
| 4,998,268 | 3/1991 | Winter | 378/63 |
| 5,012,506 | 4/1991 | Span et al. | 378/152 |

OTHER PUBLICATIONS

Calculation and Application of Point Spread Functions for Treatment planning with High Energy Photon Beams, *Acta Oncologica* 26 (1987) pp. 49-56, A. Ahnesjo, et al.

Methods of Image Reconstruction from Projections applied to Conformation Radiotherapy, *Phys. Med. Biol.*, 1990, vol. 35, No. 10, 1423-1434, Bortfeld, et al.

Feasibility Solutions in Radiation Therapy Treatment Planning, *Dept. of Radiation Therapy*, Univ. of PA School of Med., pp. 220-224, Altschuler, et al. (1984).

A Primer on Theory & Operation of Linear Accelerators in Radiation Therapy, *Medical Physics Pub. Corp.*, (1981) C. J. Karzmark, et al.

The Accuray Neutron 1000, A Medical Systems for Frameless Stereotoxic Radiosurgery, Accuray, Inc., J. R. Adler, et al., May 1992.

Optimization of Stationary and Moving Beam Radiation Therapy Techniques, *Radiotherapy and Ocology*, 12 (1988) 129-140, A. Brahme.

A Unified Approach to the Optimization of Brachytherapy and External Beam Dosimetry, *Int. J. Radiation Ocology Biol. Phys.*, vol. 20, pp. 859-873, Holmes, et al. (1991).

Optimization of Conformal Radiotherapy Dose Distributions by Simulated Annealing, *Phys. Med. Biol.*, vol. 34, No. 10, 1349-1370, S. Webb (1989).

A Constrained Least-Squared Optimization Method for External Beam Radiation Therapy Treatment Planning, *Med. Phys.* 11(5), Sep./Oct. 1984 pp. 659-664, G. Starkschall.

On the Use of Cimmino's Simultaneous Projections Method for Computing a Solution of the Inverse Problem in Radiation Therapy Treatment Planning, *Inverse Problems*, 4 (1988) 607-623, Y. Censor, et al.

Tomotherapy: A New Concept for the Delivery of Conformal Radiotherapy using Dynamic Compensation, Jul. 1992, Swerdloff, et al.

Progress In Medical Radiation Physics vol. 2, 1985, added by Colin Orton, Plenum Press, W. A. Jennings pp. 1-111.

*Primary Examiner*—Craig E. Church
*Attorney, Agent, or Firm*—Quarles & Brady

[57] ABSTRACT

A radiation therapy apparatus includes a compensator with moving leaves to attenuate a radiation beam and a compensator verification system to determine if the attenuating leaves are moving in accordance with desired position signals. Two radiation intensity monitoring chambers, one chamber on either side of a patient within a radiation beam, produce beam fluence data used by a computer to construct radiation absorption images and to evaluate the functionality of the compensator. The absorption image can be used for both radiation dose verification and planning of suitable subsequent therapy sessions.

15 Claims, 10 Drawing Sheets

5,394,452

VERIFICATION SYSTEM FOR RADIATION THERAPY

This invention was made with United States Government support awarded by the National Institute of Health (NIH), Grant Nos. NCI R29 CA48902 and NIH Training Grant NRSA CA09206. The United States Government has certain rights in this invention.

FIELD OF THE INVENTION

This application is a continuation in part of a patent application Ser. No. 07/854,521, filed Mar. 19, 1992, entitled "Method and Apparatus for Radiation Therapy".

This invention relates generally to radiation therapy equipment for the treatment of tumors, or the like, and specifically to a mechanism for verifying radiation intensity directed at, and the dose of radiation absorbed within, irregularly shaped zones of a patient.

DESCRIPTION OF THE ART

Medical equipment for radiation therapy treats tumorous tissue with high energy radiation. The dose and the placement of the dose must be accurately controlled to insure both that the tumor receives sufficient radiation to be destroyed, and that damage to surrounding and adjacent non-tumorous tissue is minimized. In order to control the radiation dose, knowledge about radiation beam intensity during a therapy session is necessary. In addition, in cases where therapy protocol requires multiple therapy sessions, verification of a radiation dose after a therapy session and data indicating the effect of the verified dose is important for planning accurate and suitable subsequent radiation doses.

In co-pending application Ser. No. 07/854,521, entitled "Method and Apparatus for Radiation Therapy", an improved radiation therapy architecture is described in which the freedom of movement of the radiation source about the patient is limited to rotation within a single gantry plane.

The architecture described in the above application employs a radiation source constrained to rotate within a single gantry plane about a patient while the intensities of individual rays of the radiation beam are modulated by a set of opaque leaves which move into and out of the radiation beam. The leaves are closed at each gantry angle for a predetermined percentage of time. By employing appropriate planning techniques the dose absorbed by each slice of the tumor may be controlled to irradiate even tumors having a concave cross section within the gantry plane.

An entire tumorous volume may be treated by moving the patient with respect to the gantry plane and irradiating each tumor slice separately. The compensator and gantry configuration together substantially increase the ability to conform a radiation dose to an arbitrarily shaped tumor while employing a simplified two-dimensional protocol.

Besides simplifying the irradiation protocol, a single plane configuration provides a number of other benefits. These benefits include the ability to use a single ring gantry to support both a radiation source and a CT system, the advantage of reduced interference between the radiation source and patient (or table) and the advantage of simplified shielding requirements. Furthermore, the simplified architecture enables a therapist to employ a helical scanning method to smoothly irradiate along the length of a tumor so as to avoid irradiation hot spots or irradiation gaps.

Despite the advantages of constraining a-therapy machine to operation with a single plane, a single plane machine presents various problems.

First, there is the need for dose verification. The destructive potential of a radiation beam to healthy tissue and the necessity of insuring that tumorous tissue receives sufficient radiation makes treatment verification a required part of radiation therapy. With conventional therapy machines, films may be exposed during a therapy session both to confirm the location of an irradiated area and to provide a record of radiation dose. Because the radiation source employed by the above described gantry configuration constantly sweeps around a gantry to produce a moving beam, a film verification system employing traditional film movement techniques would be unworkable. The verification problem is more profound if scanning is performed in a helical manner.

In addition, a single plane system must employ a compensator capable of varying the intensity of individual rays of a beam in order to properly treat a tumor. The reliability of such a compensator must be extremely high—even a single improperly attenuated beam ray passing through the compensator undetected and irradiating healthy tissue due to a failed compensator component could result in severe damage to healthy tissue.

SUMMARY OF THE INVENTION

The present invention provides a verification system that can be used in conjunction with a radiation intensity compensator to minimize the possibility of an uncontrolled beam ray irradiating nontumorous tissue. In one embodiment, the verification system may collect tomographic data on absorbed radiation within the patient and generate tomographic absorption images therefrom. These images may be used for radiation dose verification as well as for planning subsequent therapy sessions.

Specifically, the radiation compensator has a radiation source for producing a radiation beam directed toward a patient at a gantry angle, the beam including a plurality of adjacent rays. An attenuator disposed between the radiation source and the patient independently controls the fluence of each ray of the beam according to signals indicating desired ray fluences.

A pre-patient monitor disposed between the attenuating means and the patient, having a plurality of adjacent monitor segments subtended by adjacent rays of the beam produces a measured signal for each monitor segment proportional to the fluence subtending the segment. A comparator compares the desired signal to the measured signal to produce a difference value. A limiter produces an error signal if the difference value is outside a predetermined error range.

Thus, a first object of the invention is to verify how accurately the intensity of each ray of the beam is being controlled by the compensator. Large discrepancies between the measured and desired signals indicate a malfunction.

A high signal may also be produced indicating that the measured signal is too high relative to the desired signal yet within the predetermined error range and a low signal may be produced indicating that the measured signal is low relative to the desired signal yet within the predetermined error range. The compensator control receiving these signals may adjust the attenuation means to reduce a second ray fluence at a second gantry angle in response to receiving a high signal and to increase a secondary ray fluence at a second gantry angle in response to a low signal.

Another object of the invention is to provide a system which can compensate for deviations in ray fluence by adjusting ray fluence at later angles. The effect of the difference between a desired signal and the measured signal can be reduced as the radiation from the two angles combine.

In one embodiment, the attenuating means is a plurality of radiation attenuating leaves in a support structure positioned generally between the radiation source and the patient. The support structure guides the leaves between a closed state within the radiation beam, each leaf thus occluding one ray of the beam, and an open state outside of the radiation beam to allow unobstructed passage of the ray.

A motivator independently moves each leaf between the open and closed states to effect an open-to-closed desired ratio producing the fluence of each ray. The motivator may be a first set of actuators connected by linkages to individual leaves to move the leaves with the movement of the armatures.

A position sensor determines when each leaf is in the open state and when each leaf is in the closed state and produces an actual ratio of the period of time the leaf is in the open state to the period of time the leaf is in the closed state. An error detector generates an error signal by comparing the actual ratio to the desired ratio.

Another object of the invention is to provide a mechanical compensator system with extremely high reliability. The error signal generated by the error detector may be used to indicate a malfunction.

Alternatively, a second set of actuators may be connected to the leaves and when an error signal is generated by the position sensor, the control means may shut off the first actuators and employ the second actuators to resume switching within a few milliseconds. Once an actuator from the second plurality is operating, if it malfunctions and a leaf therefore fails to move as expected, the error detector may indicate that the leaf is malfunctioning.

A post-patient monitor is generally disposed opposite the pre-patient monitor with respect to the patient and within the fan beam for determining a post-patient fluence of each ray of the beam exiting the patient. An absorption calculator compares the pre-patient fluence to the post-patient fluence to produce an absorption value for each ray, the absorption values together providing an absorption profile for the fan beam at a given gantry angle.

Yet another object of the invention is to provide a record of radiation dose distributed to a tumor site. This dose record may be used by a radiotherapist to verify radiation dose throughout the volume of a tumor. In addition, the dose record reduces the possibility that interruptions in a therapy session will require termination of the session. Sessions can resume where they were interrupted. Furthermore, the dose record may be used in planning suitable subsequent therapy sessions.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

DETAILED DESCRIPTION OF THE PREFERRED EMBODIMENT

Figure 1:
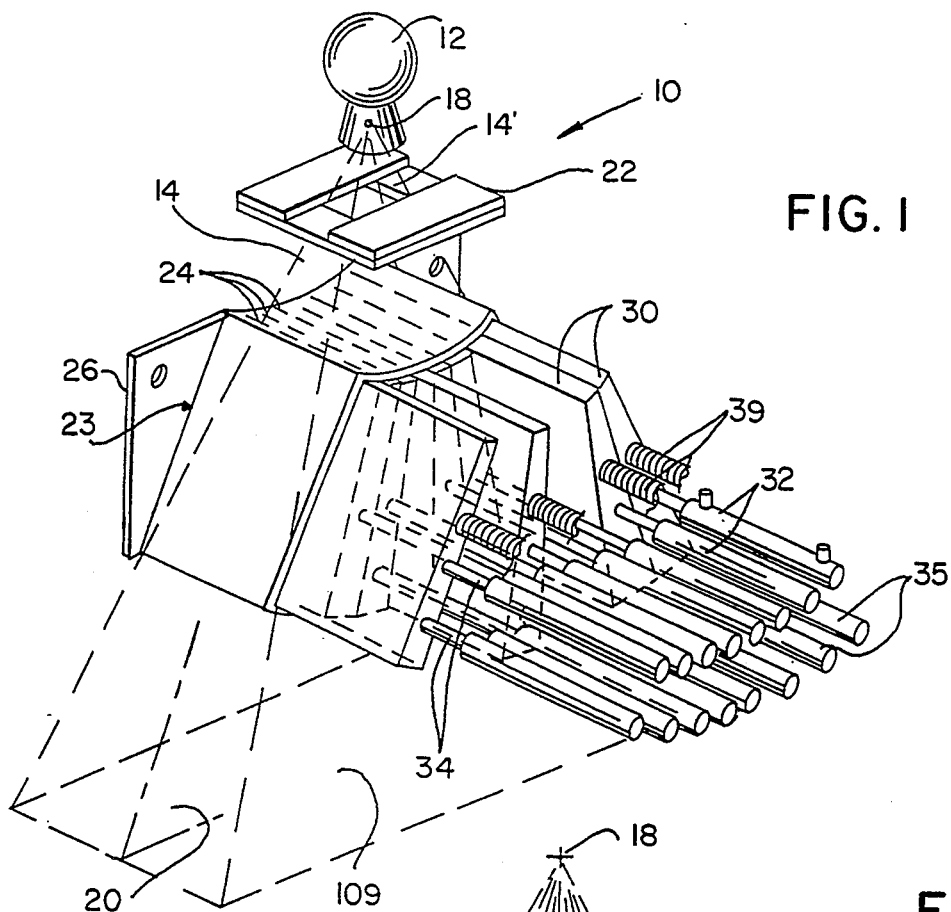
FIG. 1 is a perspective view of the compensator assembly used in the present invention, showing the compensator leaves and their associated electromagnetic actuators.

Referring to FIG. 1, a radiation therapy unit 10 suitable for use with the present invention includes a radiation source 12 producing a generally conical radiation beam 14' emanating from a focal spot 18 and directed towards a patient 17 (not shown in FIG. 1). The conical beam 14' is collimated by a radiation opaque mask 16 constructed of a set of rectangular collimator blades to form a generally planar fan beam 14 centered about a fan beam plane 20.

I. The Compensator

A compensator 22 is centered in the fan beam 14 and about the fan beam plane 20, prior to the radiation being received by the patient 17, and includes a plurality of adjacent trapezoidal leaves 30 which together form an arc of constant radius about the focal spot 18. The leaves 30 are held in sleeves 24. The sleeves 24 are constructed of radio-translucent materials and attached at their inner ends 23 to a mounting plate 26 which is fixed relative to the focal spot 18. The mounting plate 26 is constructed of a sturdy, radiopaque material and is positioned just outside the fan beam 14 to prevent interference with the fan beam 14.

Figure 2:
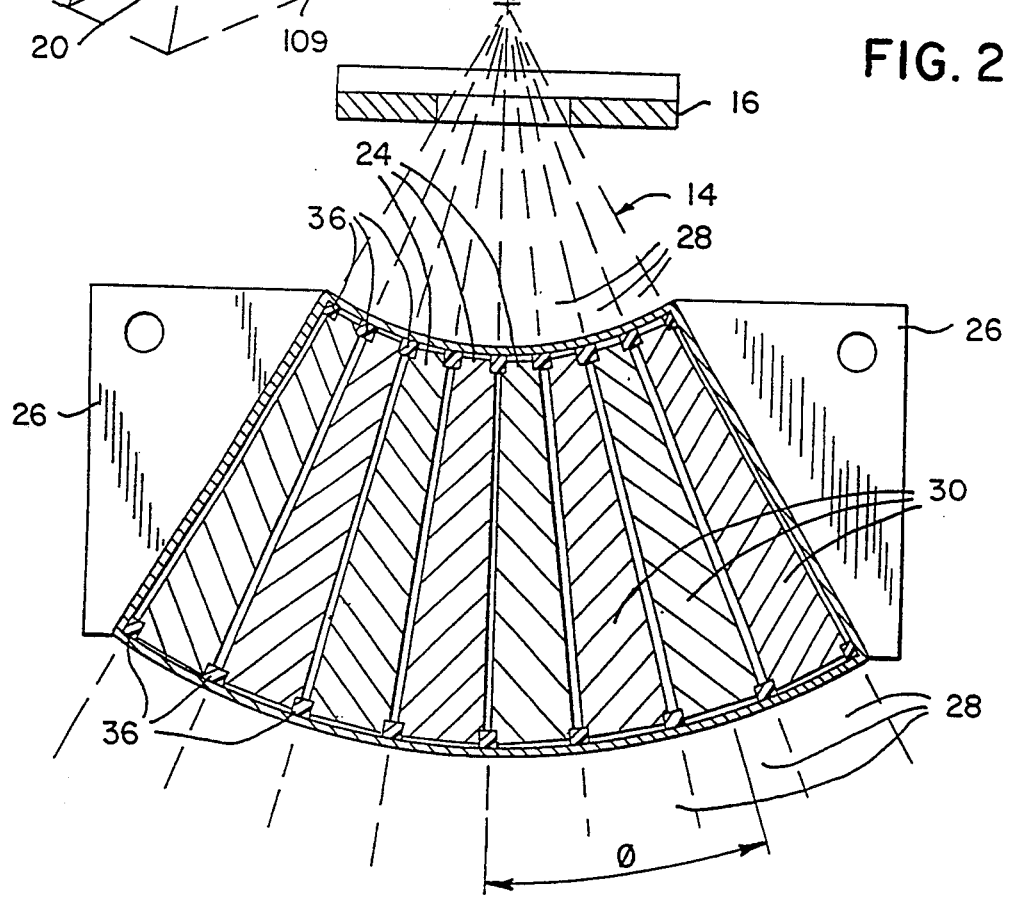
FIG. 2 is a cross section of the compensator assembly of FIG. 1 along line 2—2 showing the trapezoidal aspect of each compensator leaf, for a fan beam of radiation, and the guide rails for supporting the compensator leaves when they move.

Preferably, the leaves 30 of the compensator 22 subtend the entire fan beam 14 to divide the fan beam 14 into a set of adjacent slab-like rays 28 at offset angles f. Referring also to FIG. 2, each sleeve 24 is open at its outer end 27 to receive, by sliding, a comparably sized trapezoidal leaf 30 constructed of a dense, radiopaque material such as lead, tungsten, cerium, tantalum or a related alloy.

Each leaf 30 may slide completely within its corresponding sleeve 24 to block the ray 28 associated with that sleeve 24. When the leaf 30 blocks its corresponding ray 28, it is referred to as being in a "closed state". The sleeves 24 are of ample length to permit each leaf 30 to slide out of the path of the fan beam 14, so as to leave its corresponding ray 28 completely unobstructed, and yet to still be guided by the sleeve 24. In this non-blocking position, a leaf is referred to as being in the "open state".

Each leaf 30 moves rapidly between its open and closed states by means of a primary corresponding relay-like electromagnetic actuator 32 connected to the leaf 30 by a slider member 34. The actuators 32 have internal armatures (not shown) received within solenoid electromagnets. The armature may be moved at high velocity by means of varying electrical excitations of their associated electromagnets. The electrical excitations are provided by a compensator control (not shown in FIGS. 1 or 2) to be described below. The actuators 32 are capable of applying high forces to the leaves 30 to move them rapidly and independently between the open and closed states.

Each leaf 30 is also provided with a back up actuator 35 located below its primary actuator 32 on the outer edge of the leaf 30. The secondary actuator 35 is employed when the primary actuator 32 fails as will be described in more detail below.

Figure 3:
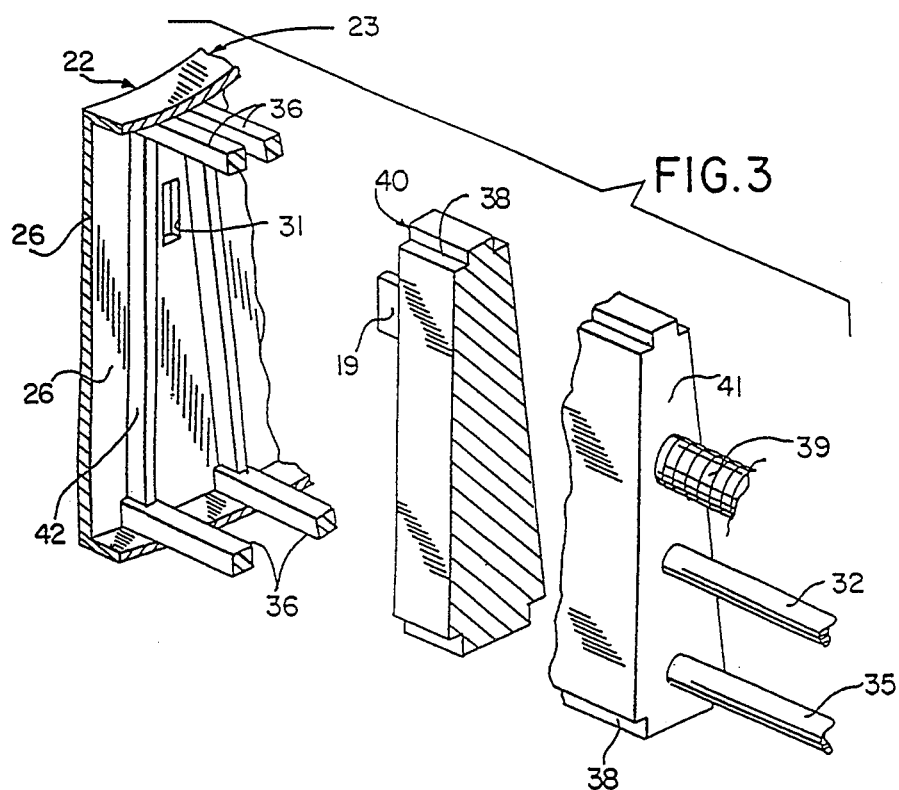
FIG. 3 is a cutaway perspective view of a set of guide rails and one leaf of FIG. 2 showing a collar for supporting the leaf.

Referring now to FIGS. 2 and 3, the leaves 30 are supported and guided within the sleeves 24 by guide rails 36 fitted into notches 38 cut along the edges of the leaves 30. The notches 38 allow the guide rails 36 to slidably retain the leaves 30 within the sleeves 24 during motion between the open and closed states.

In the closed state, the inner end 40 of each leaf 30 is captured by a rigid collar 42 attached to the mounting plate, which aligns the leaf 30, more accurately than may be done by the guide rails 36, with the mounting plate 26 and hence with the fan beam 14. Whereas the guide rails 36, which are ideally radiotranslucent, are relatively insubstantial, in contrast, the collar 42, positioned outside the fan beam 14 on the mounting plate 26, need not be radio-translucent and hence is more substantial in construction. A collar (not shown) similar to collar 42, supports each leaf 30 when it is fully in the open state. Because the leaves 30 spend most of their time fully in the open or closed states, they are, at most times, firmly located by a supporting collar 42.

Of concern is the reliability of leaf 30 switching because one inoperable leaf 30 would prevent treatment. The number of switching cycles S (opening and closing) in a year is given by the following equation:

$$S = 250 \frac{\rho LB}{\Delta z}$$

where 250 is typical of the number of treatment days per year in North America and $\rho$ is the number of patients treated per day. S is going to be on the order of millions of cycles per year.

If the probability of a single leaf 30 failing in a year is $P_1$ then the probability of any leaf within the system failing P is given by:

$$P = 1 - (1 - P_1)^n$$

where n is the number of leaves 30. Since the leaves 30 are light, the slide member 34 is under little stress and so it has a low probability $P_{slide}$ of failure.

Figure 4:
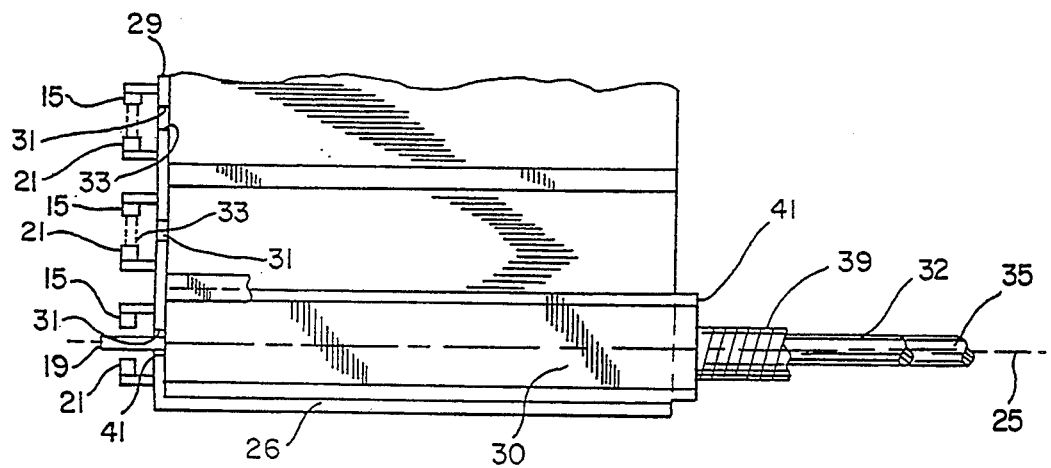
FIG. 4 is a plan view of a portion of the mounting rack and one leaf of FIG. 1 showing a trigger bore, a trigger and a light emitting diode and light detector pair with the leaf in its fully closed position.

Referring now to FIGS. 3 and 4, a light opaque trigger member 19 is integrally attached to the inner edge 40 of each leaf 30, the trigger member 19 extending laterally outward parallel to the movement axis 25 of each leaf 30. When the leaf 30 is in the closed state (see FIG. 4), the trigger member 19 passes through a trigger bore 31 in the back wall 29 of the mounting plate 26.

A plurality of light emitting diode 21 and light detector 15 pairs are positioned on the outer surface of the back wall 29, the elements of each pair opposing each other on opposite sides of an associated trigger bore 31. When a leaf 30 is in the closed state, its associated trigger member 19 extends through the trigger bore 31 and blocks the light path 33 between the light emitting diode 21 and light detector 15. Referring to FIG. 3, when the leaf 30 is not in the closed state, the trigger member 19 does not extend through the trigger bore 31 and hence light passes from the emitting diode 21 to the light detector 15. The probability of the light detector 15 failing is $P_{verify}$.

An axially compressible spring 39 is provided between the outer edge 41 of each leaf 30 and the front wall (not shown) of the mounting plate 26 to move the leaf 30 to the closed position absent force from its actuator 32. A system employing a light detector 15, primary and backup actuators 32, 35 and which are regularly serviced, would have downtime due to failure of a leaf 30 according to the probability equation:

$$P_1 = 1 - (1 - P_{slide})(1 - P_{verify}) \left[ 1 - \left( \frac{P_{actuator}}{N_{maint}} \right)^2 \right]$$

wherein $P_{actuator}$ is the probability of the actuator or control electronics failing during a year and $N_{maint}$ is the number of maintenance services in the year (e.g. it could be every day). The exponent 2 accounts for the failure of both actuators in the maintenance period. This equation basically says that failure of a leaf 30 will happen if the slider 34 fails, the verification system fails or both of the actuators 32, 35 fail before the system can be serviced.

Figure 5:
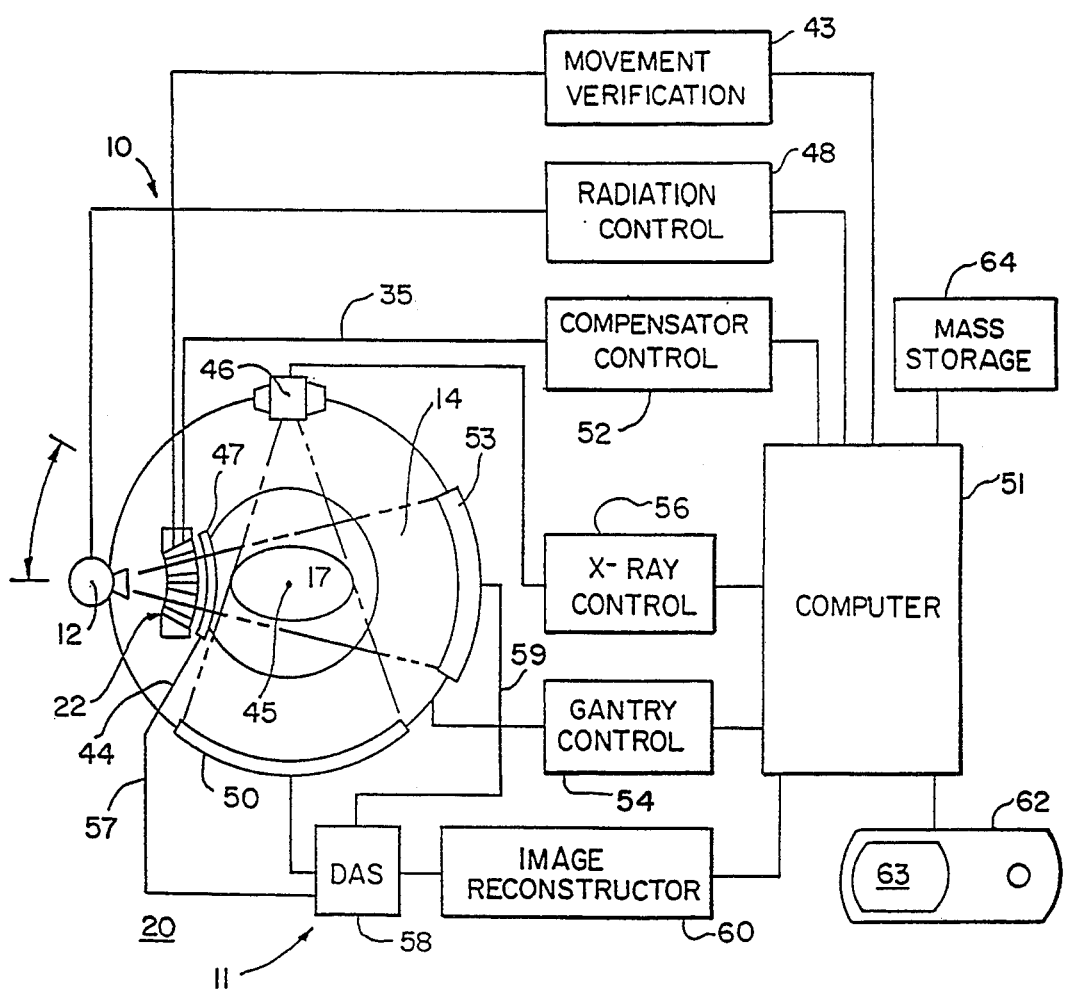
FIG. 5 is a block diagram showing the elements of a radiation therapy apparatus incorporating a conventional CT scanner and the compensator of the present invention and including a computer suitable for controlling that compensator per the present invention.
Figure 14:
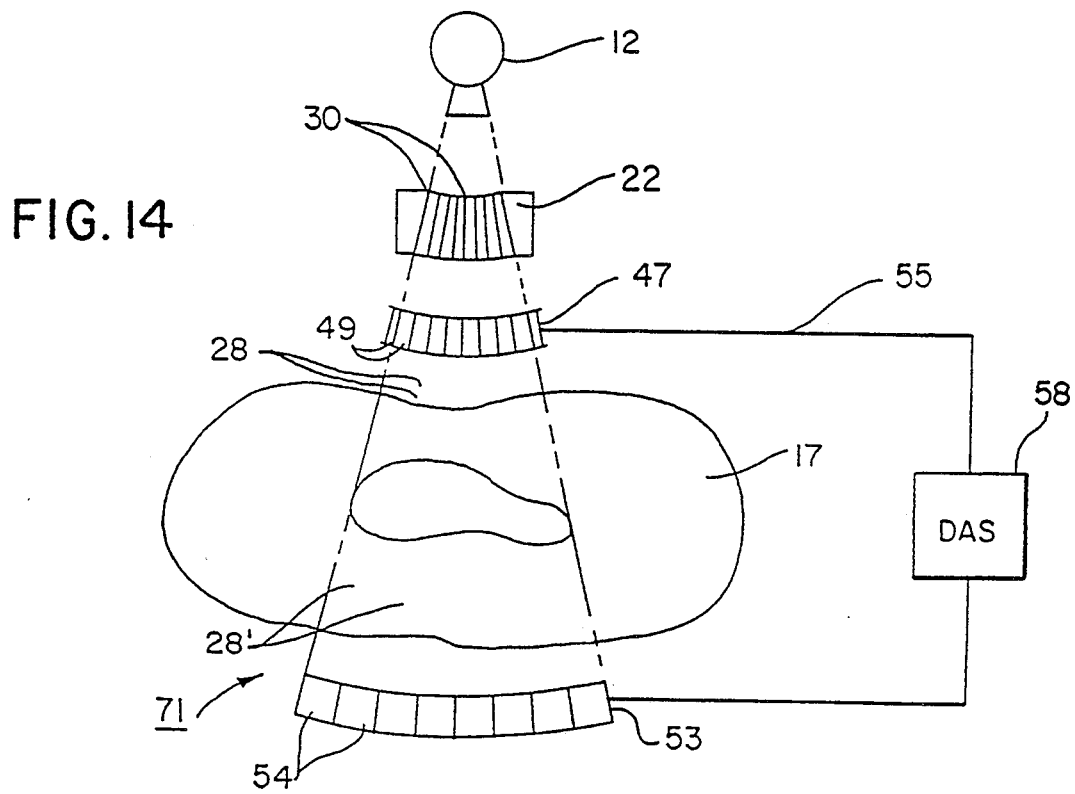
FIG. 14 is a schematic view showing the general orientation of the monitoring chambers in relation to the compensator and the patient.

Referring to FIGS. 5 and 14, a pre-patient multi-segment ion chamber 47 is positioned between the compensator 22 and the patient 17. Each ray 28 of the fan beam 14 subtends a separate monitor segment 49 as it passes through the ion chamber 47. A post-patient multi-segment ion chamber 53 is positioned directly opposite the radiation source 12 on the gantry 44 so as to intercept the fan beam 14 as it exits the patient 17. The separate monitor segments 54 of the second ion chamber 53, like the monitor segments 49 of the first ion chamber 47, are each subtended by individual rays 28 of the fan beam 14'. The ion chambers 47, 53 produce signals indicating the fluence of rays 28 (as generally understood in the art) and as used by the computer 51 to determine radiation dose in a manner to be described below.

II. Radiation Therapy Hardware

Referring now to FIG. 5, the radiation source 12 is mounted on a gantry 44, the latter rotating within the fan beam plane 20 about a center of rotation 45 in the patient 17 so that the fan beam 14 may irradiate a slice of the patient 17 from a variety of gantry angles $\theta$. The radiation source 12 is controlled by a radiation control module 48 which turns the radiation beam 14 on or off under the control of a computer 51.

A compensator control 52 directed by a timer generating desired position signals provides electrical excitation to each electromagnet to control, separately, the actuators 32 to move each of the leaves 30 in and out of its corresponding sleeve 24 and ray 28 (see also FIG. 1). The compensator control 52 moves the leaves 30 of the compensator 22 rapidly between their open and closed states to either fully attenuate or provides no attenuation to each ray 28. Gradations in the fluence of each ray, as needed for each fluence profile, are obtained by adjusting the relative duration during which each leaf 30 is in the closed position compared to the relative duration during which each leaf 30 is in the open position, for each gantry angle.

The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below. The compensator control 52 also connects with computer 51 to allow program control of the compensator 22 to be described.

A tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planning purposes. Alternatively, such tomographic imaging may be performed on a separate machine and the slices aligned according to fiducial points on the patient 17.

A gantry control module 54 provides the signals necessary to rotate the gantry 44 and hence to change the position of the radiation source 12 and the angle $\theta$ of the fan beam 14 for the radiation therapy, as well as for the computed tomography x-ray source 46 and detector array 50 also attached to gantry 44. Gantry control module 54 connects with computer 51 so that the gantry may be rotated under computer control and also to provide the computer 51 with a signal indicating the gantry angle q to assist in that control.

Control modules for the tomographic imaging system 11 include: x-ray control module 56 for turning on and off the x-ray source 46, and data acquisition system 58 for receiving data from the detector array 50 in order to construct a tomographic image.

An image reconstructor 60 receives the data from the data acquisition system 58 in order to assist in "reconstructing" a tomographic treatment image from such data according to methods well known in the art. The image reconstructor 60 also communicates with computer 51 to assist in high speed computations used in the present invention as will be described below. The tomographic treatment image allows verification of the patient setup just prior to radiation therapy treatment. An image reconstructor 60 typically comprising a high speed array processor or the like may use the actual fluence signals 57 and barrier signals 59 to produce a tomographic absorption image to be used for verification and future therapy planning purposes as described in more detail below.

A terminal 62 comprising a keyboard and display unit 63 allows an operator to input programs and data to the computer 51 and to, control the radiation therapy and tomographic imaging equipment 10 and 11 and to display tomographic images produced by the image reconstructor 60 on the display 63.

A mass storage system 64, being either a magnetic disk unit or tape drive, allows the storage of data collected by the tomographic imaging system 11 and the multi-segment ion chambers 47, 53 for later use. Computer programs for operating the radiation therapy system 10 will generally be stored in mass storage unit 64 and loaded into the internal memory of the computer 51 for rapid processing during use of the system 10.

During operation of the radiation therapy unit 10, the compensator control 52 receives from the computer 51 a fluence profile for each gantry angle. The fluence profile describes the intensity or fluence of each ray 28 of the radiation beam 14 that is desired for that gantry angle $\theta$ at a given position of the patient support table (not shown) as translated through the radiation beam 14. The collection of fluence profiles over a range of rotation gantry angles is termed a "treatment sinogram".

III. Therapy Planning Software

The generation of a treatment sinogram needed to obtain the full benefits of the above described compensator is performed by specially developed software running on the computer 51 and reconstructor 60. Although the treatment planning is performed in software, it will be recognized that the planning may also be implemented in discrete electronic circuitry dedicated to this operation and that such dedicated circuitry may be employed to provide even greater speed to this process.

Figure 6A:
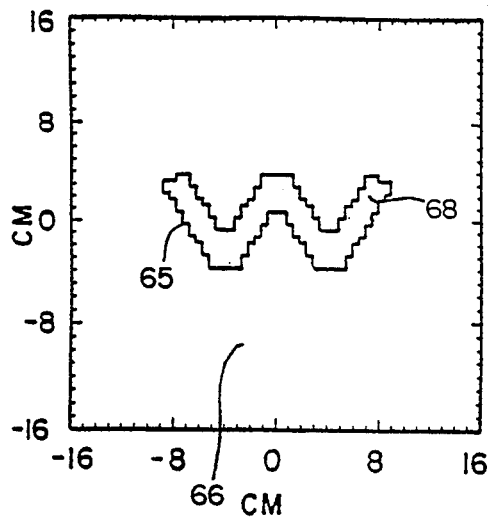
FIGS. 6(a)-(d) are dose distributions of a hypothetical tumorous region showing dose intensity by lines of equal dose, with FIG. 6(a) showing a desired dose distribution and FIGS. 6(b), (c), and (d) showing progressive actual dose distributions after two, three and ten iterations per present invention.
Figure 6B:
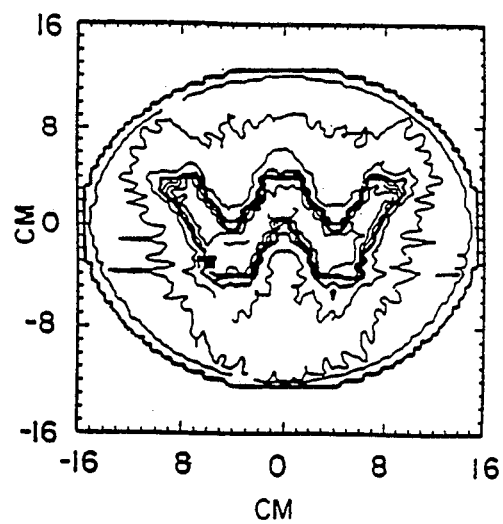

Referring to FIG. 6(a), the generation of the desired treatment sinogram to control compensator 22 begins with the definition of a desired dose map 66. A typical desired dose map 66 assigns a relatively high radiation dose, within a dose constraint, to an area of tumorous tissue 68 and a second lower radiation dose to the area of healthy tissue 70 outside of that region. The healthy tissue 70 may include an area 72 including a radiation sensitive organ or the like to which an even lower radiation dose may be assigned.

The desired dose map 66 is stored within the memory of computer 51 as an array of elements each element holding one digital value, and may be most easily entered by displaying the tomographic view of the slice of patient 17 on the display 63 of the terminal 62 and manually tracing around the tumorous area 68 using a trackball or a similar input device as is well understood in the art. Standard area-filling computer programs may be used to transfer the dose values assigned to each traced region to the appropriate element in the array of memory representing the desired dose map 65.

Each element of the dose map 66 thus defines the dose desired at each of the plurality of volume elements 74 ("voxels") within a slice of the patient 17. Referring to FIG. 6, each voxel 74 of the patient 17 may be identified by a vector $\vec{r}$ defined from a given reference point 76. The dose at each voxel 74 is $D(\vec{r})$.

A. Converting Dose to Terma

1. Terma

Generally, the dose at any voxel $\vec{r}$ will depend on the energy received at that voxel $\vec{r}$ from radiation scattered from adjacent voxels $\vec{r}$ (where adjacent voxels $\vec{r}$ include the voxel $\vec{r}$, i.e., the radiation received directly from the radiation source 12). The dose $D(\vec{r})$ for a given voxel e,rar/r/ is given by the following formula:

$$D(\vec{r}) = \int T(\vec{r'}) A(\vec{r}-\vec{r'}) d^3\vec{r'} \quad (1)$$

where $T(\vec{r'})$ is a value indicating the magnitude of the primary total energy released from $\vec{r'}$ per unit mass of that voxel $\vec{r'}$ and is called the "terma" (total energy released per unit mass).

For a monoenergetic external radiation source, the terma rate $\dot{T}(\vec{r})$ is described by:

$$\dot{T}(\vec{r}) = \frac{\mu}{\rho}(\vec{r}) E \int \phi(\vec{r}) dt \quad (2)$$

where $\mu/\rho$ is an effective mass attenuation value at the voxel $\vec{r'}$, E is the energy of the radiation photons in Joules, $\phi$ is the distribution of the fluence rate (flux density). The integration of energy times fluence rate over time is energy fluence $\Psi(\vec{r'})$ where:

$$\Psi(\vec{r}) = E \int \phi(\vec{r}) dt \quad (3)$$

hence $$T(\vec{r}) = \frac{\mu}{\rho}(\vec{r}) \psi(\vec{r}) \quad (4)$$

Equation (4) basically relates how much energy from the ray 47 interacts with the voxel r'.

2. Convolution Kernel $A(\vec{r}-\vec{r'})$ is a convolution kernel describing non-stochastic energy transport or scattering in a uniform medium. $A(\vec{r}-\vec{r'})$ thus describes how the energy from each voxel $\vec{r'}$ spreads to contribute to the dose at voxel $\vec{r}$.

The kernel $A(\vec{r}-\vec{r'})$ may be generated using a Monte Carlo method as is generally understood in the art. As mentioned, it is a three-dimensional function indicating the fraction of energy absorbed at voxel $\vec{r}$ per unit of energy released at voxel $\vec{r'}$. The energy emitted from the terma of each voxel $\vec{r'}$ finds its source in a directed ray 47 from external radiation source 12 and thus $A(\vec{r}-\vec{r'})$ is generally anisotropic as suggested in FIG. 8, spreading outward away from the entry of ray 28. Energy conservation requires that:

$$\int A(\vec{r'}) d^3\vec{r'} = 1.0 \quad (5)$$

That is, if the energy transferred by the primary interaction were all deposited on the interaction point, the kernel would be approximated as a delta function.

Figure 8:
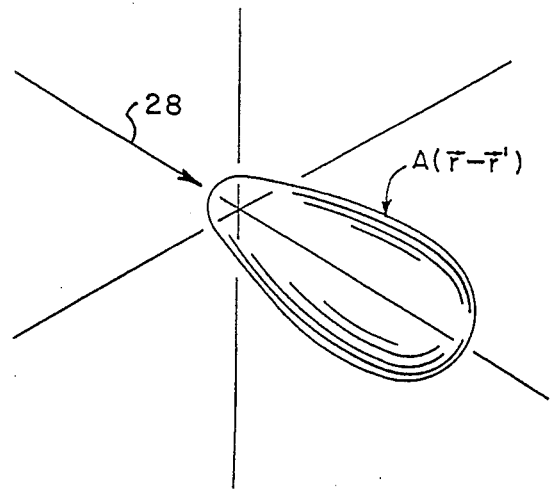
FIG. 8 is a perspective representation of a monodirectional scatter kernel associated with a radiation beam at one gantry angle.

Referring still to FIG. 8, the anisotropy of $A(\vec{r}-\vec{r'})$ is related to the gantry angle $\theta$ and thus of the angle of incidence of the ray 28 at $\vec{r'}$. If the gantry angles q at which the patient 17 is irradiated are predetermined, a multidirection convolution kernel $B(\vec{r}-\vec{r'})$, shown in FIG. 9, may be created from weighted superimposition of the kernels $A(\vec{r}-\vec{r'})$.

Figure 9:
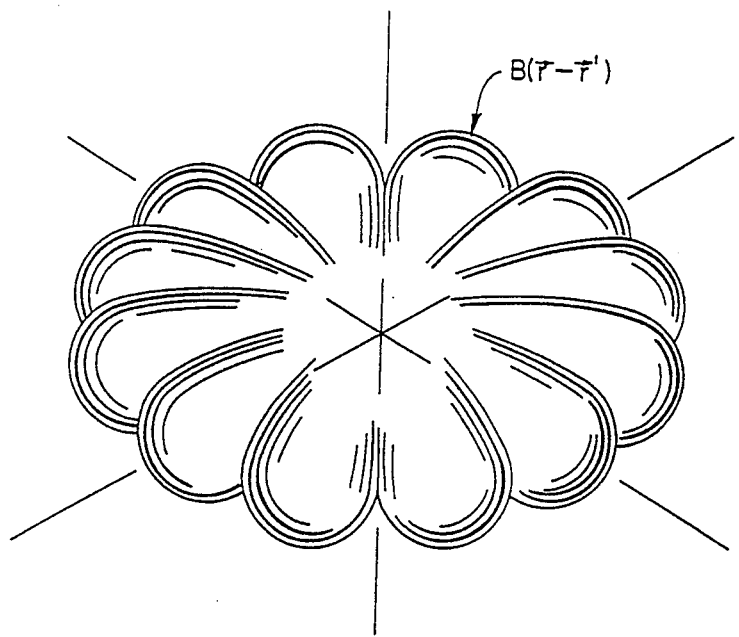
FIG. 9 is a perspective representation of a composite multidirectional scatter kernel associated with a plurality of radiation beams at multiple gantry angles.

Referring to FIG. 9, assuming that the spreading of radiation is approximately equal for all beam directions and the rays 28 from each gantry angle q contribute equally to the terma at voxel $\vec{r'}$, then the multidirectional convolution kernel reduces to a "isotropic" form as follows:

$$B(\vec{r} - \vec{r'}) = \frac{1}{n} \sum_{i=1}^{n} A(\vec{r} - \vec{r'})_i \quad (6)$$

where n is the number of discrete gantry angles from which rays 28 are projected.

For multiple rays 28 at different gantry angles, the total dose at a given voxel $\vec{r}$ is the sum of doses from each constituent beam, therefore:

$$D(\vec{r}) = \int T(\vec{r'}) B(\vec{r}-\vec{r'}) d^3\vec{r'} \quad (7)$$

where $T(\vec{r'}) = n T(\vec{r'})_i$, the latter term being the contributed portion of the terma for the ith gantry angle.

This simplification assumes that the contribution to the terma from each ray 28 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r'}$ to calculate the dose over the entire patient volume. Preferably, therefore, the calculational efficiency of the fast Fourier transform can be used and equation (7) converted to the following:

$$D(\vec{r}) = F^{-1}\{F\{T(\vec{r'})\} \cdot F\{B(\vec{r}-\vec{r'})\}\} \quad (8)$$

where F and $F^{-1}$ symbolize Fourier and inverse Fourier transforms respectively. This simplification of equation (8) requires that the kernel $B(\vec{r}-\vec{r'})$ be spatially invariant and relies on the convolution theorem which states that convolution of two spatially invariant quantities in a space domain is equivalent to multiplication in the frequency domain.

The assumption of the spatial invariance of $B(\vec{r}-\vec{r'})$ is correct only to a first order approximation. Typically, the kernel $B(\vec{r}-\vec{r'})$ for an external radiation source 12 is a complex function of: (1) beam hardening of a polyenergetic x-ray beam (i.e., the effect of the filtration of the patient 17 in increasing the proportion of high frequency or high energy radiation components), (2) the number of rays 28 crossing each voxel, and (3) exponential attenuation by the patient mass.

In the preferred embodiment, this first factor, beam hardening, is neglected because it is an effect smaller than the attenuation problem. Thus, the photon energy spectrum in the patient 17 may be assumed to be the same as that of the external radiation source 12. This simplification is not required, however, and it will be understood that beam hardening could be accurately accounted for by representing a photon energy spectrum by a finite number of separately convolved energy intervals.

The second factor, the difference in the number and orientation of rays 28 that cross each voxel, caused by the geometry of a finite number of gantry angles and the fan orientation of the beam 14, affect spatial invariance. Problems arising from the fan orientation of the beam (in contrast to a parallel beam geometry) are largely solved if there is a full rotation of the gantry 44. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-\vec{r}')$ is assumed to be spatially invariant and the dose calculated according to equation (8).

Production of terma values from a desired dose map 75 is then simply the process of inverting equation (8) as follows:

$$T(\vec{r}) F^{-1}\left( \frac{F\{D(\vec{r})\}}{F\{B(\vec{r}-\vec{r}')\}} \right) \quad (9)$$

This inversion requires that there be no significant "zeros" (typically at high frequencies) in the denominator term $F\{B(\vec{r}-\vec{r}')\}$ or more simply that the kernel $B(\vec{r}-\vec{r}')$ be spatially compact (i.e., the Fourier transform of a spatially compact kernel will have significant high frequency content). It has been determined by the present inventors that the kernels dictated for patients 59 are sufficiently compact to allow this Fourier deconvolution.

Figure 10:
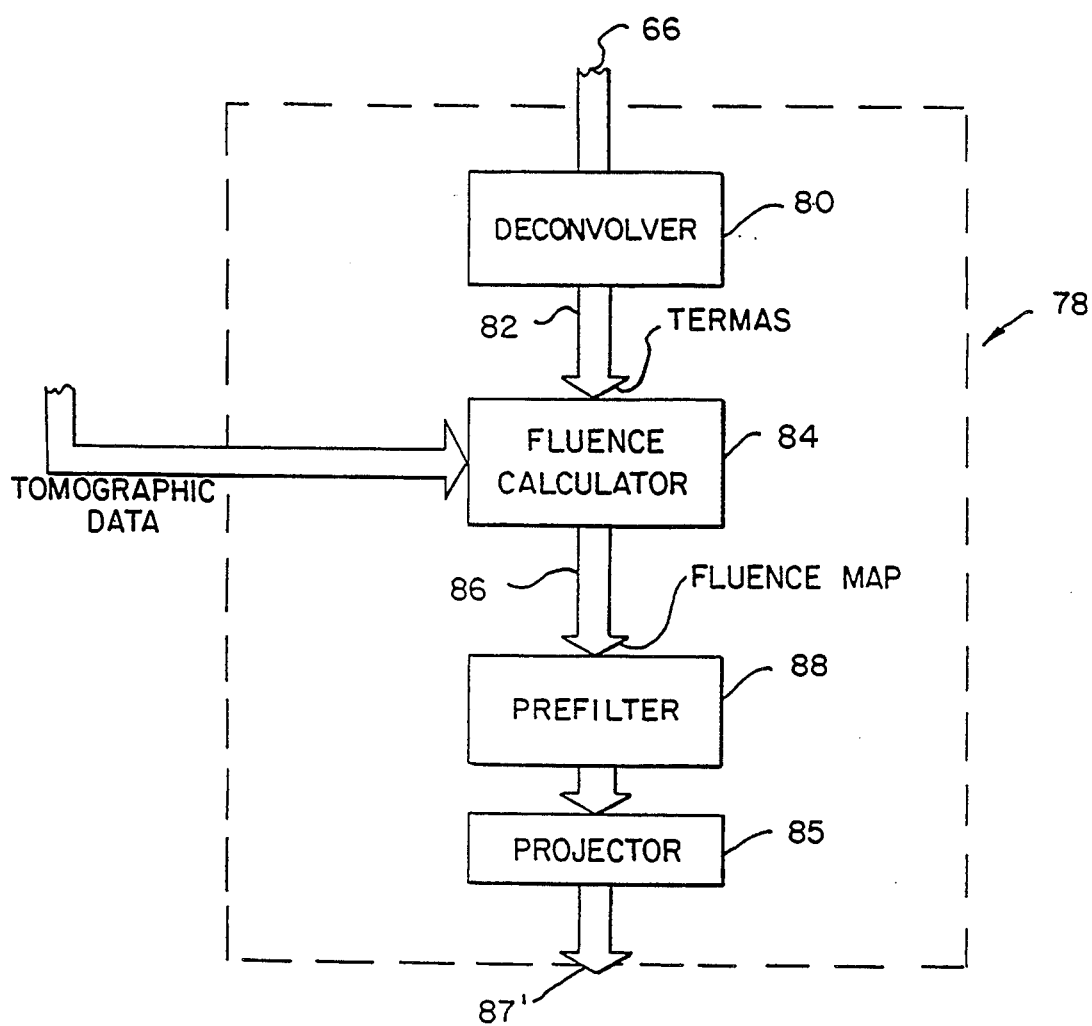
FIG. 10 is a block diagram depicting the fluence profile calculator which takes a desired dose map and calculates a fluence profile.

Referring now to FIG. 10, this deconvolution to produce a terma map 82, giving the terma for each voxel $\vec{r}$, from the desired dose map 66, is represented by process block 80.

B. Converting Terma to Voxel Energy Fluence

Knowing the terma map 82, the energy fluence $\Psi(\vec{r}')$, which is a measure of the beam intensity, can be determined at each corresponding voxel by equation (4) from a knowledge of m/r as follows:

$$\psi(\vec{r}) = \frac{T(\vec{r})}{\frac{\mu}{\rho}(\vec{r})} \quad (10)$$

The value of $\mu/\rho$ may be estimated and considered a constant or actual m/r may be deduced from the tomographic scan data collected by means of the tomographic imaging system 60, (shown in FIG. 5). In this manner and as illustrated by process block 84 of FIG. 10, a fluence map 86 giving the fluence at each point of the terma map may be determined.

C. Converting Voxel Energy Fluence to Energy Fluence Profile

The energy fluence $\Psi(\vec{r}')$ at each voxel $\vec{r}'$ is related to the energy of the ray 28 exiting the compensator 22 by the relation:

$$\psi(\vec{r}) = \psi_0(\phi,\theta) \, e^{-\int \mu/\rho(\vec{r})\rho(\vec{r})\delta(p - \hat{r}\cdot\vec{r})dt} \left( \frac{SSD^2(\phi,\theta)}{|\vec{t}|^2} \right) \quad (11)$$

where $\Psi_0(\phi,\theta)$ is the energy fluence for a given ray 28 as described by $\delta(p-\hat{r}\cdot\vec{r}')$ at the exit of the compensator 22 and serves to define the fluence profile of the compensator and $\theta$ and $\phi$ are the gantry angle and the offset angles of the ray 28 as previously described.

The exponential term represents the attenuation of the ray 28 from the exit of the compensator 22 to the voxel $\vec{r}$ caused by the mass of the patient 59 where by $\mu/\rho(\vec{r})$ is the attenuation for each voxel $\vec{r}$ along the ray 28, $\rho(\vec{r})$ is the density of each voxel $\vec{r}$, SSD($\phi,\theta$) is the distance between the exit of the compensator 22 and the surface of the patient 17, r is a unit vector along $\vec{r}$ (where the origin of is now assumed. to be the center: of rotation of the gantry 44), and p is the perpendicular distance from the gantry's center of rotation 45 and the ray 28. The vector is simply a vector along the ray 28 to provide an integration variable.

The fluence at each voxel $\vec{r}$ is related to the fluence of the radiation beam 14 emitted from the compensator 22 by equation (11). In the preferred embodiment, the density and attenuation of each voxel $\vec{r}, \mu/\rho(\vec{r})$ and $\rho(\vec{r})$ are assumed to be constant and the fan beam of radiation is approximated by a parallel beam, hence $$\frac{SSD^2(\phi,\theta)}{|\vec{t}|^2} = 1.$$

Borrowing from the mathematics of tomographic image reconstruction, the fluence map 86 may be "reverse" back projected (i.e. projected) by projector 85 to determine a fluence profile to be produced by the external-source necessary to generate the desired fluence map and hence dose.

This projection is simply the opposite of a typical back projection used to form an image of a tomographic slice of a patient 17 front a series of projections taken in a tomographic imaging system. Because a projection is a line integral across a distribution, the energy fluence distribution for each voxel (equation (11)) is first differentiated with respect to the rayline $\vec{t}$:

$$\frac{d\psi(\vec{r})}{dt} = \left[\frac{\mu}{\rho}(\vec{r})\rho(\vec{r})\delta(\rho - \hat{r}\cdot\vec{r}) + \frac{2}{t}\right]\psi(\vec{r}) \tag{12}$$

The line integral of $$\frac{d\psi(\vec{r})}{dt} \text{ along } \vec{t},$$

corrected for attenuation and inverse-square falloff, then represents the projection operation and $\Psi_0(\phi, \theta)$, the fluence profile over the offset angles $\phi$ of each gantry angle $\theta$, is:

$$\psi_0(\phi,\theta) = \int \left[\frac{\mu}{\rho}(\vec{r})\rho(\vec{r})\delta(\rho - \hat{r}\cdot\vec{r}) + \frac{2}{t}\right] \times (\psi(\vec{r}) \, e^{+\int \mu/\rho(\vec{r})\rho(\vec{r})\delta(\rho-\hat{r}\cdot\vec{r})d\vec{t}}\left(\frac{|\vec{t}|^2}{SSD^2(\phi,\theta)}\right)\rightleftharpoons\delta(\rho - \hat{r}\cdot\vec{r})d\vec{t} \tag{13}$$

The projection of equation (13) is represented by projector 85 in FIG. 10.

The projection process, for the purpose of computing fluence profiles for the compensator 22, differs in a fundamental way from the simple inverse of tomographic back projection. The difference is primarily in a concern for the sharpness in the transition of the dose between the irradiated tumorous tissue 68 and the healthy tissue 70. Sharpness in this transition region reduces the irradiation of healthy tissue 70 and is preferred over actual fidelity of the dose to the desired dose map 66.

For this reason, the fluence map 86 from the fluence calculator 84 is prefiltered as shown by process block 88 to produce a filtered fluence map $\Psi'(\phi, \theta)$ as follows:

$$\Psi'(\phi,\theta) = F^{-1}\{F\{\Psi(\phi,\theta)|\omega|\}_+ \tag{14}$$

where $\Psi(\phi,\theta)$ is the fluence map 86 and $|\omega|$ is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile.

In practice the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation $$\Psi(\phi,\theta) = \wp\{D(\vec{r})\} \otimes I(t) \tag{15}$$

where $\wp$ prefers to a projection operation and $I(t)$ is the fast inversion filter. The $\otimes$ operators refers to a convolution operation such as would normally be done in Fourier space using a fast Fourier transformation.

Referring still to FIG. 10, the fluence profile calculations of block 78, including the deconvolver 80, the fluence calculator 84, the prefilter 88 which includes any projection space filter (such as a ramp filter, a fast inversion filter followed by truncation of zeros), and the projector 85 thus produce fluence profiles which together create an estimated treatment sinogram 87' from the desired dose map 66. The fluence profile calculator 78 may use the Fourier convolution of equation (9) in the estimate of the fluence profiles at this stage, accepting minor inaccuracies in that process, to be corrected at a later stage, as will be described below.

D. Iteration

Figure 11:
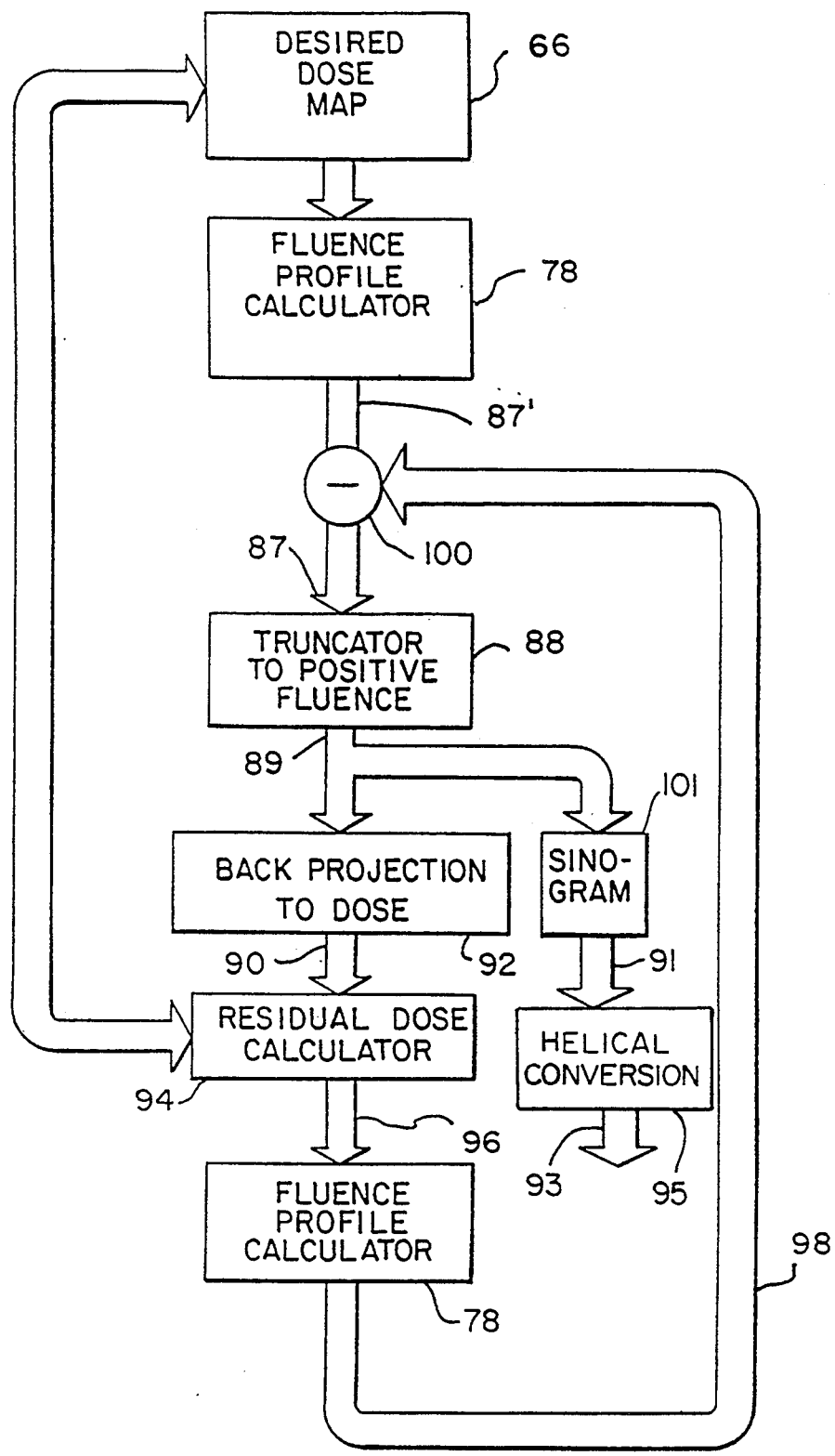
FIG. 11 is a block diagram depicting the overall iterative method of controlling the compensator of the present invention, employing the fluence profile calculation method of FIG. 10.

Referring now to FIG. 11, the fluence profile calculator 78 converts the desired dose map 66 to an estimated treatment sinogram 87', however the fluence profiles of this estimated treatment sinogram 87' may not be used to control the compensator 22 because, in general, the estimated treatment sinogram 87' will include positive and negative values of fluence. Only positive values of fluence are physically realizable by the compensator 22; a negative value of fluence would represent a ray 28 that absorbed radiation along its path which is physically unrealizable.

Accordingly, at process block 88, the fluence values of the estimated treatment sinogram 87' are truncated to positive fluence values 89. As a result of this truncation, the estimated treatment sinogram 87° no longer produces the desired dose map.

The amount of error resulting from the truncation producing the positive fluence profiles 89 is determined by back-projecting the positive fluence values 89 to an actual dose map, 90 deviating from the desired dose map 66. This back projection is accomplished by computing a fluence map from the positive fluence values 89 per equation (11) and a terma map per equation (4) and then convolving the terma map with the kernel per equation (7) to establish the actual dose map 90 per process block 92 of FIG. 11.

In this back projection, the assumption of spatial invariance of the convolution kernel $B(\vec{r}-\vec{r}')$ is not made so as to produce a more accurate actual dose map 90.

The projection of a fluence profile onto a patient 17 to compute a dose map may be performed by a number of other procedures known to those of ordinary skill in the art.

The actual dose map 90 is compared to the desired dose map 66 to produce residual dose map 96 as indicated by process block 94. In the preferred embodiment, the comparison subtracts from the values of each voxel $\vec{r}$ of the actual dose map 90, the greater of: a) the corresponding value of desired dose map 766, or b) a predetermined upper dose constraint. The predetermined upper dose constraint is a threshold number that is deemed an acceptable dose to tumorous tissue 76. Clearly, other methods of quantifying the difference between the desired dose map and the actual dose map will be apparent, from this description, to those of ordinary skill in the art.

Figure 12:
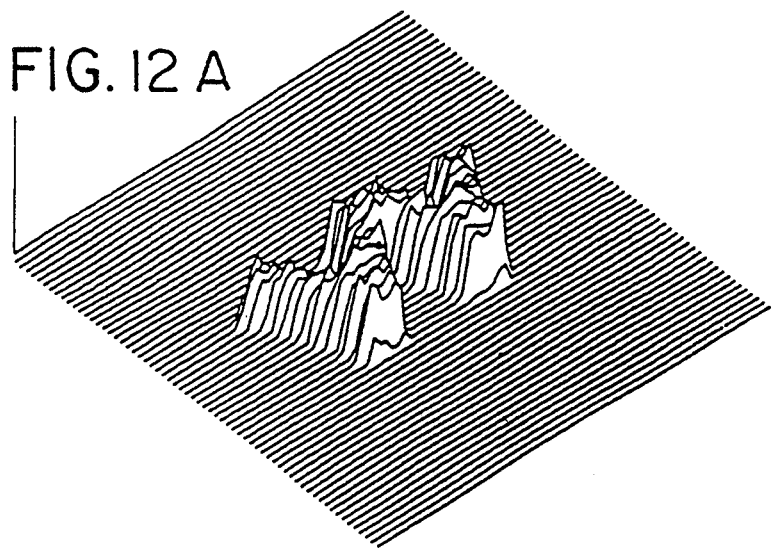
FIGS. 12(a)-(c) are perspective views of plots showing the error between the desired dose distribution and the actual dose distribution obtained with the present invention for one, two and four steps of iteration respectively.
Figure 12:
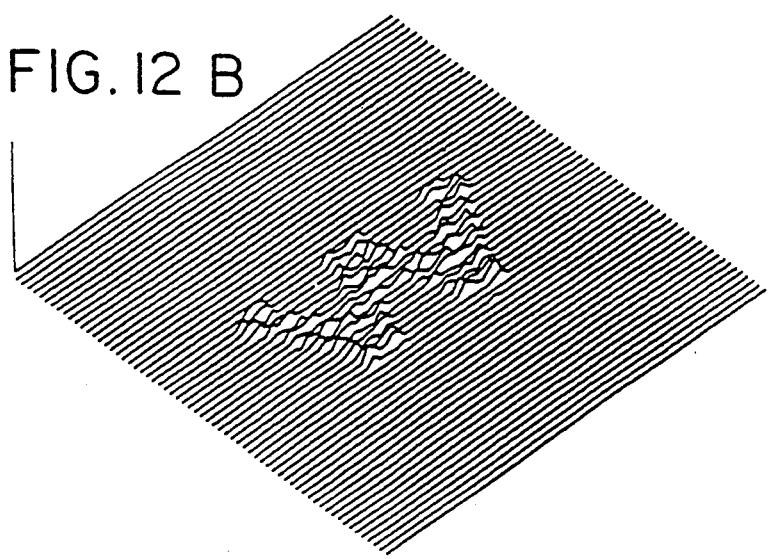
Figure 12:
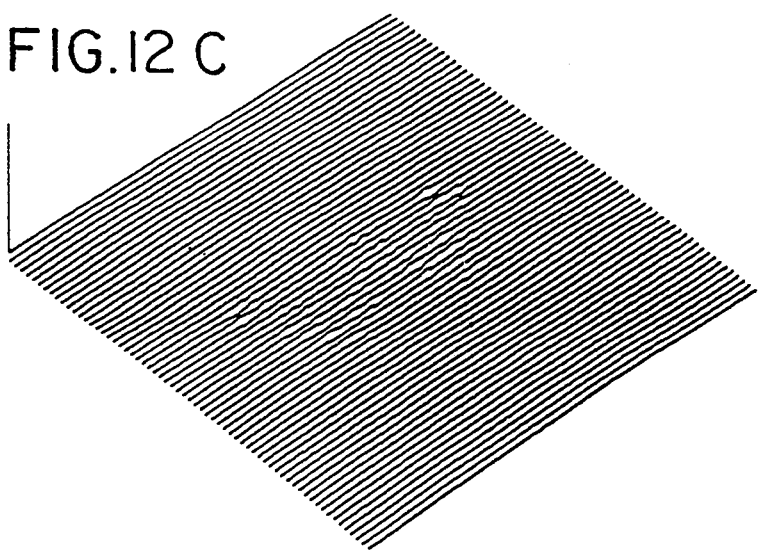

The result of this comparison process 94 is to produce a residual dose map 96 shown in FIG. 12(a). This residual dose map 96 is then, again, operated on by the fluence profile calculator 78 (in lieu of the desired dose map 66) to produce an error fluence profile 98 (in lieu of the estimated treatment sinogram 87).

A thus produced error fluence profile 98 is subtracted by subtracter 100 from the estimated treatment sinogram 87' to produce a new estimated treatment sinogram 90.

As shown in FIG. 11, this new estimated treatment sinogram 87 is repeatedly operated on by process blocks 88, 92, 94 and 78 for a predetermined number of iterations, the magnitude of the error fluence profile 98 values decreasing with each iteration as shown in FIGS. 12(b)–(c) until a suitably low error fluence profile 98 is obtained.

The new estimated fluence profile 87 is then truncated per process block 88 to produce a final sinogram 91 for use in controlling the compensator 22, as previously described.

Figure 6C:
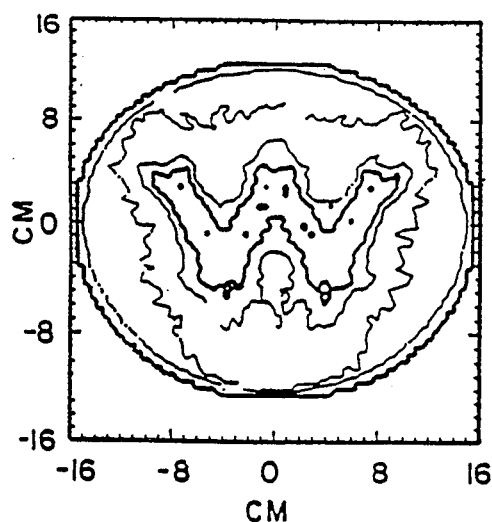
Figure 6D:
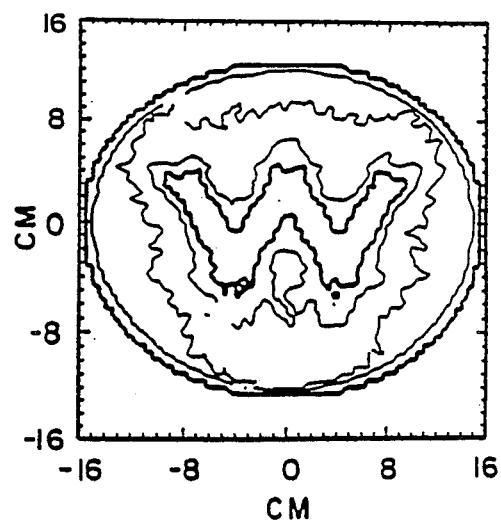

Referring again to FIGS. 6(b), (c) and (d), dose maps obtained by the present invention corresponding to a desired dose map 66 of FIG. 6(a) are shown after: one iteration (FIG. 6(b)); two iterations (FIG. 6(c)); and ten iterations (FIG. 6(d)). The variations in dose in the target volume shown in FIG. 6(d) are plus or minus 2% about the predetermined upper limit of 1,000 cGy.

E. Converting Slice Data To Helical Data

In order to eliminate radiation hot spots and radiation gaps along the length of a tumor, helical scanning, in which the translation table is continuously moved along a "z axis" through the gantry 44 as the gantry 44 rotates so that the radiation fan beam 14 sweeps a helical pattern through the tumor site, is desirable. Helical scanners also reduce irradiation time because the start and stop motion of the translation table is eliminated. Nevertheless, because of the constant translation of the patient during helical scanning, the treatment sinogram, as discussed above, must be modified.

Figure 13A:
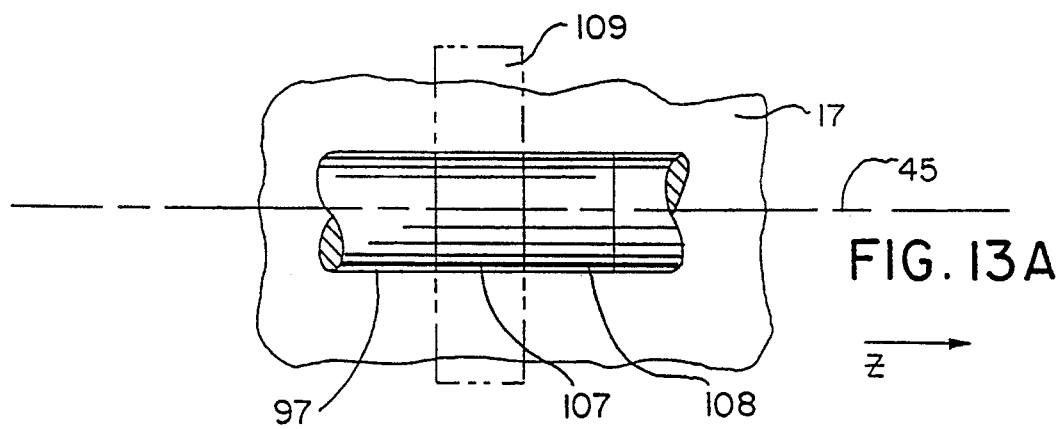
FIGS. 13(a)-(c) are schematic views showing the relationship between an irradiation window and adjacent tumor slices as the radiation source rotates about the gantry from 0° to 90° to 180°.
Figure 13B:
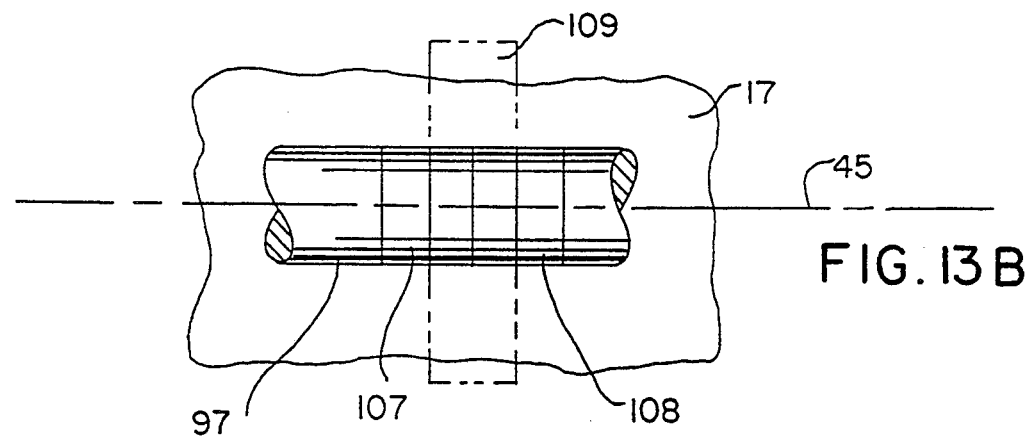
Figure 13C:
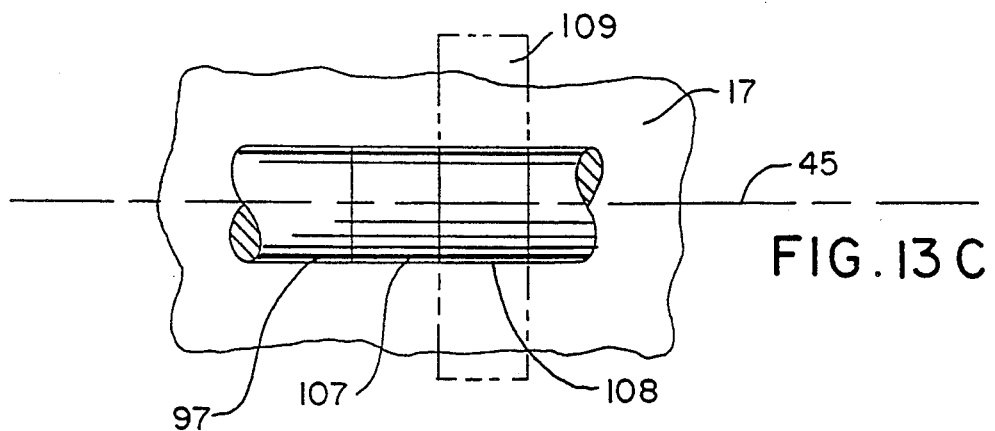

Referring to FIGS. 13(a)–(c), a simplified cylindrical tumor 97 with its axis coincident with the axis of rotation 45 of the gantry 44 has been divided into separate slices 107, 108. An irradiation window 109 collimated by the opaque mask 16 (shown in FIG. 1) subtends different portions of the tumor 97 as the tumor 97 is translated through the gantry 44 and the radiation source 12 rotates about the tumor 97.

In a helical scan the irradiation window 109 subtends multiple adjacent slices (i.e. it is not slice specific). Referring to FIG. 13(a) at a 0° gantry position, the irradiation window 109 may irradiate only slice 107. As the tumor 97 is translated and the radiation source 12 rotated, the irradiation window 109 begins to subtend parts of both slice 107 and adjacent slice 108. Referring to FIG. 13(b), after 90° of rotation, the irradiation window 109 may subtend half of slice 107 and half of slice 108. Referring to FIG. 13(c), after 180° of rotation, the irradiation window 109 only subtends slice 108. Therefore, helical or non-slice specific data must be developed from the slice sinograms 91 in order to control the compensator leaves 30 during helical irradiation.

Although different portions of a tumor may have different cross sections or density distributions, if slice data is generated that corresponds to many thin tumor slices, the changes in the tumor between adjacent slices will be small. Under these circumstances, fluence profiles for adjacent tumor slices directed along identical gantry angles $\theta$ will be substantially similar. Therefore interpolation between adjacent fluence profiles sharing an identical gantry angles $\theta$ may be made without appreciably sacrificing irradiation accuracy.

To convert the final slice sinograms 91 to a continuous fluence profile "ribbon" 93 for easy use in helical scanning, a helical conversion module 95 (see FIG. 11) may use the following weighted averaging equation to make adequate helical fluence profile approximations:

$$\psi(z_1, z_2, \theta_j) = \psi(z_1, \theta_j)\left(1 - \frac{\theta_j}{180}\right) + \psi(z_2, \theta_j)\left(\frac{\theta_j}{180}\right) \quad (16)$$

where $z_1$ is the first of two adjacent slices, $z_2$ is a second adjacent slice, $\theta_j$ is the gantry angle, $\Psi(z_1, z_2, \theta_j)$ is the fluence profile of the fan beam 14 directed so as to subtend adjacent portions of tumor slices $z_1$ and $z_2$ from gantry angle $\theta_j$, $\Psi(z_1,\theta_j)$ is the fluence profile from the final slice sinogram 91 corresponding to slice $z_1$ from gantry angle $\theta_j$ and $\Psi(z_2,\theta_j)$ is the fluence profile from the slice sinogram 91 corresponding to slice $z_2$ from gantry angle $\theta_j$. $\theta_j=0°$ when the fan beam subtends only slice $z_1$ and changes as the gantry rotates until the fan beam subtends only adjacent slice $z_2$ after 180° of rotation. Therefore, at $\theta_j=0°$ (see FIG. 13(a)) only $\Psi(z_1,\theta_j)$ will influence $\Psi(z_1, z_2,\theta_j)$. At $\theta_j=90°$, (see FIG. 13(b)) when the translation table has moved the tumor 97 one half of a slice thickness so that one half of the fan beam 14 is directed at slice $z_2$, one half of $\Psi(z_2,\theta_j)$ and one half of $\Psi(z_1,\theta_j)$ will influence $\Psi(z_1, z_2,\theta_j)$.

After the fluence profile ribbon 93 is generated, it is stored in the mass storage system 64 for later use during a therapy session.

IV. Operation Of The Verification System

Prior to a therapy session, the fluence profile ribbon 93 for controlling the compensator 22 is loaded into the compensator control 52. The ribbon 93 consists of a plurality of fluence profiles to be directed at the tumor from a sequence of gantry angles $\theta$ as the translation table moves through the gantry 44. Each fluence profile consists of desired intensity data for each ray 28 of the fan beam 14. The compensator control 52, directed by the fluence profile ribbon 93 data, drives the leaves 30 into and out of the radiation beam 14 effecting various radiation intensities as described above.

Referring to FIGS. 3, 4 and 5, as the compensator control 52 drives the leaves 30 between the open and closed states, the trigger member 19 of each leaf 30 is driven in and out of its associated light path 33. When the trigger member 19 blocks the light path 33 (i.e. the leaf 30 is in the closed state), the light detector 15 produces an actual position signal indicating that the leaf 30 is in the closed position. When the trigger member 19 is outside the light path 33 (i.e. the leaf 30 is in the open state), the light detector 15 produces an actual position signal indicating that the leaf 30 is in the open state.

An error detector (not shown) realized in software runs on the computer 51 and compares the actual position signals to the desired position signals generated by the compensator control 52 to identify mistakes in leaf 30 movement. If a leaf 30 fails to assume the position indicated by a desired position signal, the compensator control 52 assumes that the actuator 32 failed.

Upon failure of an actuator 32, the compensator control 52 directs its signals so as to bypass the primary actuator 32 and begin to direct the backup actuator 35. Thus, a level of redundancy is added to the system wherein failure of a leaf movement means will not require delay in therapy protocol.

In the event that both actuators 32, 35 fail, the spring 39 biases the leaf 30 into the closed state, the leaf 30 thus occluding its associated ray 28. In this manner the possibility of a leaf 30 becoming stuck in an open state so that an uncontrolled ray 28 is directed at the patient is reduced.

The system can be equipped with an alarm to indicate when one or both of the actuators 32, 35 has failed. However, even upon failure of both actuators 32, 35 associated with the same leaf 30, a therapy session can continue once the leaf 30 is biased into its closed position. A closed leaf 30 poses no danger of radiation overexposure because the associated beam ray 28 is entirely occluded. The deficiency in actual radiation absorbed by the tumor because of leaf 30 failure can be compensated for in later therapy sessions.

Referring now to FIG. 14, there is shown a simplified compensator 22 and verification system 71 wherein the compensator 22 has only eight attenuating leaves 30 dividing the fan beam 14 into eight adjacent rays 28.

As part of a treatment verification system 59, the first multisegment ion chamber 47 disposed between the compensator 22 and the patient 17 has eight chamber segments 49, each segment 49 directly within one of the eight rays 28 of the fan beam 14. Each segment 49 produces a measured ray fluence signal 55, or pre-patient fluence signal indicative of the ray fluence encountered thereby.

The second multisegment ion chamber 53 disposed within the fan beam 14 opposing the radiation source 12 on the opposite side of the patient 17 consists of a second group of eight chamber segments 54, each segment 54 intercepting one ray 28' that passes through the patient 17. These chamber segments 54 produce post-patient fluence signals 57 indicative of the fluence of rays 28' that have traversed the thickness of the patient 17.

Figure 15:
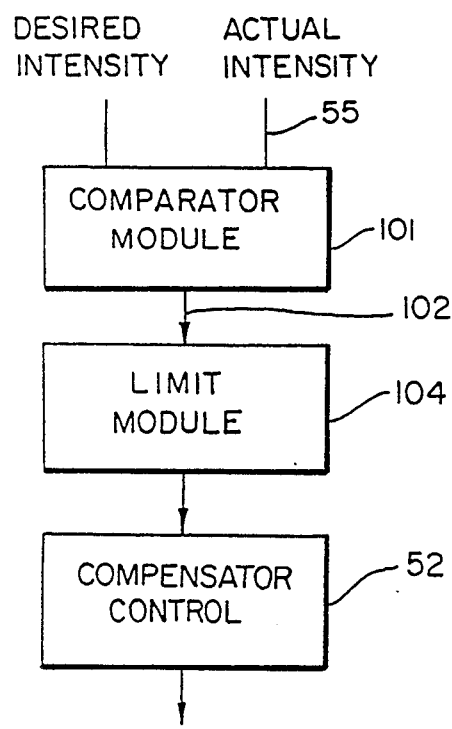
FIG. 15 is a block diagram depicting the fluence modulation method of changing leaf ratios to adjust ray fluences.

The measured ray fluences 55 are employed by the verification system 71 for two distinct purposes. First, referring to FIG. 15, a comparator module 101 receives from the computer 51 the desired ray fluence to be generated by every leaf 30 of the collimator 22. In addition, the comparator module 101 (see FIG. 15) receives the measured ray fluence 55 generated by the first ion chamber 49. Comparing the desired ray fluence to the measured ray fluence 55, the comparator module 101 generates a difference value 102 for each leaf 30 at each gantry angle $\theta$.

A limit module 104 determines if the difference value 102 is outside of a reasonable limit and dangerous to the patient. If so, the compensator control 52 turns off both the primary 32 and backup 35 actuators for the duration of the therapy session. With the actuators 32, 35 turned off, the biasing spring 39 (see FIG. 4) forces the leaf into the closed position to occlude the ray 28 and eliminate possible radiation danger.

If the difference value 102 is minimal or the measured ray fluence 55 is less than the desired ray fluence, the difference can be corrected by adjusting the ray intensity of second ray 28 and a different gantry angle.

Figure 7:
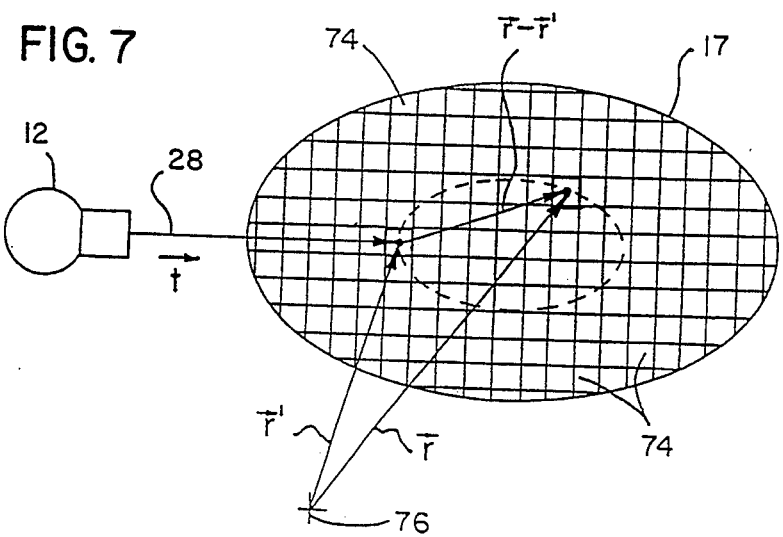
FIG. 7 is a diagrammatic representation of a patient receiving radiation therapy, showing the scatter kernel and the coordinate system used to describe the present invention.

Referring to FIG. 7, and as described above, the total radiation absorbed by a voxel 74 of the tumor being the summation of radiation directed along many rays 28 toward the voxel 74, discrepancies between desired ray fluence and measured ray fluence 55 can be corrected by adjusting the fluence of the second ray 28 adjacent the first ray. Decreasing fluence of a second ray 28 reduces the quantum of total radiation delivered to a voxel 74. Likewise, increasing fluence of the second ray 28 increases the quantum of total radiation delivered to a voxel 74. In this manner, relatively minor discrepancies between desired and measured ray fluences can be eliminated resulting in more accurate therapy sessions.

Second, the measured ray fluence signals 55 are used in conjunction with the post-patient fluence signals 57 to produce tomographic absorption images. By knowing the fluence of each ray 28 entering the patient 17 and the fluence of each ray 28' exiting the patient 17, a simple subtraction calculation generates an absorption value indicating how much radiation is absorbed by the tissue within the patient 17 traversed by the ray 28. By combining all of the rays 28 directed along a gantry angle $\theta$ while the translation table is in a single position, an absorption profile for that angle $\theta$ and table orientation can be constructed.

Data collected during a helical therapy session in which a fan beam 14 sweeps a helical pattern through a tumor site is not slice specific. Because it is most advantageous to view tomographic images as slices rather than as a helix, the helical data is converted to slice specific data.

The computer 51 employs the helical conversion module 95 for a second time to convert the helical data into slice fluence data. Because each tumor slice shares absorption profiles with two adjacent tumor slices (one before and one after), the following weighted averaging equation may be employed:

$$\psi(z_2, \theta_j) = \qquad (17)$$

$$\psi(z_1, z_2, \theta_j)\left(\frac{\theta_j + 180}{180} - 1\right) + \psi(z_2, z_3, \theta_j)\left(\frac{360 - \theta_j}{180}\right)$$

where $z_1$ is a first tumor slice, $z_3$ is a second tumor slice, $z_2$ is a third tumor slice between $z_1$ and $z_3$, $\Psi(z_2,\theta_j)$ is the absorption profile for tumor slice $z_2$ at gantry angle $\theta_j$, $\Psi(z_1,z_2,\theta_j)$ is the absorption profile detected between adjacent portions of slices $z_1$ and $z_2$ at gantry angle $\theta_j$ and $\Psi(z_2,z_3,\theta_j)$ is the absorption profile detected between slices $z_2$ and $z_3$ at gantry angle $\theta_j$ where $\theta_j$ varies between 0° and 360°.

After slice absorption profiles corresponding to the various gantry angles $\theta$ have been calculated for each tumor slice, tomographic reconstruction techniques may be used to produce a plurality of slice specific tomographic absorption images to be viewed on the display unit 63.

Standard isodose curve data used in the art for therapy planning purposes can be used by the computer 51 to establish various levels of radiation absorption along the depth of the tissue traversed by each ray 28.

By back-projecting a plurality of absorption profiles (one profile for every gantry angle $\theta$ at which the beam 14 was directed toward a slice) and simultaneously accounting for the levels of radiation absorption within each ray 28, a tomographic absorption image can be constructed in a manner similar to that used in tomographic x-ray imaging.

A radiologist can use the tomographic absorption images to determine radiation dose absorption within slices of the tumor. These images can also be used to develop more accurate diagnostic techniques and to study the specific effects of irradiation on tumor size and longevity.

The above description has been that of a preferred embodiment of the present invention. It will occur to those who practice the art that many modifications may be made without departing from the spirit and scope of the invention. For example, The image reconstructor 60 could produce a tomographic desired fluence image for comparison with the tomographic absorption image to produce a tomographic irradiation error image. The error image could then be used to repeat the helical irradiation process to correct for insufficient irradiation. Clearly the method for planning radiation therapy is not limited to a particular radiation source but may be used with any radiation source which may be decomposed into separately attenuated radiation rays. In order to apprise the public of the various embodiments that may fall within the scope of the invention, the following claims are made:

We claim:

1. In a radiation therapy machine having a radiation source for producing a radiation beam directed toward a patient at a gantry angle, the beam including a plurality of adjacent rays, a controller comprising:
   an attenuation means disposed between the radiation source and the patient for independently controlling the fluence of each ray of the beam;
   a compensator control for controlling the attenuation means according to first desired ray fluences at a first gantry angle;
   a pre-patient monitor disposed between the attenuating means and the patient having a plurality of monitor segments, adjacent monitor segments subtended by adjacent rays of the beam, each segment producing a fluence signal proportional to the measured fluence of the ray subtending the segment;
   comparison means for comparing the desired fluence of a ray to the measured fluence to produce a difference value; and
   limit means for producing an error signal if the difference value is outside of a predetermined error range.

2. The controller as recited in claim 1 wherein the limit means also produces:
   a high signal indicating that the measured fluence was too high relative to the desired fluence yet within the predetermined error range; and
   a low signal indicating that the measured fluence was too low relative to the desired fluence yet within the predetermined error range.

3. The controller as recited in claim 2 wherein the compensator control receives signals from the limit means and communicates with the attenuation means to:
   reduce a second desired fluence at a second gantry angle in response to receiving a high signal; and
   increase a second desired fluence at a second gantry angle in response to a low signal.

4. The controller recited in claim 1 wherein the attenuating means comprises:
   a plurality of radiation attenuation leaves;
   a supporting structure positioned generally between the radiation source and the patient for guiding the leaves between a closed state within the radiation beam, each leaf thus occluding one ray of the beam, and an open state outside of the radiation beam to allow unobstructed passage of the ray; and
   motivation means communicating with the control means for independently moving each leaf between the open and closed states to effect an open to closed ratio producing the desired fluence of each ray.

5. The controller as recited in claim 4 wherein the motivation means is a first plurality of actuators connected by linkages to individual leaves to move the leaves with movement of the armatures and wherein the motivation means further includes a second plurality of actuators connected by linkages to individual leaves, each actuator of the second plurality being employed when the limit means produces an error signal.

6. In a radiation therapy machine having a radiation source for producing a radiation beam directed toward a patient at a gantry angle, the beam including a plurality of adjacent rays, a controller comprising:
   a plurality of radiation attenuating leaves;
   a supporting structure positioned generally between the radiation source and the patient for guiding the leaves between a closed state within the radiation beam, each leaf thus occluding one ray of the beam, and an open state outside of the radiation beam to allow unobstructed passage of the ray;
   motivation means for independently exerting a force on each leaf to move each leaf between the open and closed state;
   compensator control communicating with the motivation means for controlling the desired ratio of the period of time during which each leaf is in the closed state to the period during which each leaf is in the open state to control the average fluence of each ray of the beam;
   a position sensor for determining when each leaf is in the open state and when each leaf is in the closed state, and producing an actual ratio of the period of time the leaf is in the open state to the period of time each leaf is in the closed state; and
   an error detector for generating an error signal by comparing an actual ratio to the desired ratio.

7. The controller as recited in claim 6 wherein the position sensor comprises:
   an opaque trigger member affixed to an edge of each leaf; and
   a light sensor disposed so that the trigger member blocks light to the sensor when the leaf is in one of the open or closed positions.

8. The controller as recited in claim 6 wherein the motivation means is a plurality of electromagnetic actuators having armatures moved by a first electrical excitation and connected by linkages to individual leaves to move the leaves with movement of the armatures and wherein the motivation means further includes a second plurality of electromagnetic actuators having armatures moved by electrical excitation and connected by linkages to individual leaves, each actuator of the second plurality being employed when the error signal indicates an error in leaf movement.

9. The controller as recited in claim 8 further including a warning means indicating when the actual ratio is infinite.

10. The controller as recited in claim 6 also including a plurality of biasing means that maintain each leaf in the closed state absent force from the motivation means.

11. The controller as recited in claim 10 wherein the biasing means is a spring.

12. In a radiation therapy machine having a radiation source for producing a radiation beam directed toward a patient at a gantry angle, the beam including a plurality of adjacent rays, the machine having an attenuating means disposed between the radiation source and the patient for independently controlling the fluence of each ray of the beam, a verification system comprising:

a pre-patient monitor generally disposed between the attenuating means and the patient for determining separately a pre-patient fluence of each ray of the beam prior to entering the patient; and a post-patient monitor generally disposed opposite the pre-patient monitor with respect to the patient and within the fan beam for determining a post-patient fluence of each ray of the beam exiting the patient.

13. The system recited in claim 12 further comprising:

an absorption calculator for comparing the pre-patient fluence to the post-patient fluence to produce an absorption value for each ray, the absorption values together providing an absorption profile for the fan beam at a given gantry angle.

14. The system recited in claim 13 further comprising:

a reconstruction means receiving absorption profiles from a plurality of gantry angles to create a tomographic absorption image of the patient.

15. The system recited in claim 12 wherein the attenuating means includes:

a plurality of radiation attenuating leaves disposed within a supporting structure generally between the radiation source and the patient for guiding the leaves between a closed state within the radiation beam, each leaf thus occluding one ray of the beam, and an open state outside of the radiation beam to allow unobstructed passage of the ray;

a motivation means for independently moving each leaf between the open and closed states; and a timing means communicating with the motivation means for controlling the ratio of the period of time during which each leaf is in the closed state to the period during which each leaf is in the open state to control the average energy fluence of each ray of the beam.

* * * * *